US009642814B2

(12) United States Patent
Ramachandran et al.

(10) Patent No.: US 9,642,814 B2
(45) Date of Patent: May 9, 2017

(54) MICROENCAPSULATION TECHNIQUE AND PRODUCTS THEREOF (71) Applicant: Likarda, LLC, Kansas City, KS (US)

(72) Inventors: Karthik Ramachandran, Shawnee, KS (US); Stephen Michael Harrington, Overland Park, KS (US)

(73) Assignee: Likarda, LLC, Kansas City, KS (US)

( * ) Notice: Subject to any disclaimer, the term of this patent is extended or adjusted under 35 U.S.C. 154(b) by 0 days.

(21) Appl. No.: 14/730,071

(22) Filed: Jun. 3, 2015

(65) Prior Publication Data

US 2015/0352056 A1 Dec. 10, 2015

Related U.S. Application Data (60) Provisional application No. 62/007,717, filed on Jun. 4, 2014.

(51) Int. Cl.
A61K 9/50 (2006.01)
A61K 9/16 (2006.01)
A61K 38/39 (2006.01)
G21K 5/02 (2006.01)

(52) U.S. Cl.
CPC .......... *A61K 9/5089* (2013.01); *A61K 9/1635* (2013.01); *A61K 9/1652* (2013.01); *A61K 9/1694* (2013.01); *A61K 9/5036* (2013.01); *A61K 38/39* (2013.01); *G21K 5/02* (2013.01)

(58) Field of Classification Search
None
See application file for complete search history.

(56) References Cited

U.S. PATENT DOCUMENTS

| 5,800,829 | A | * | 9/1998 | Dionne | A61K 9/0024 424/422 |
| 6,793,937 | B2 | | 9/2004 | Quong | |
| 8,202,701 | B2 | | 6/2012 | Boyan et al. | |
| 2012/0315307 | A1 | | 12/2012 | Henrotin et al. | |

FOREIGN PATENT DOCUMENTS

GB 2192171 * 1/1988 .............. B01J 13/02

OTHER PUBLICATIONS

El-Rehim, "Characterization and Possible Agricultural Application of Polyacrylamide/Sodium Alginate Crosslinked Hydrogels Prepared by Ionizing Radiation", Journal of Applied Polymer Science, vol. 101, pp. 3572-3580 (2006).*

(Continued)

Primary Examiner — Bethany Barham
Assistant Examiner — Barbara Frazier
(74) Attorney, Agent, or Firm — Hovey Williams LLP (57) ABSTRACT Inside-out gelation process to generate hydrogel microcapsules (aka microbeads). Methods of encapsulating biological material in the microbead 3-dimensional hydrogel matrix are described herein. The process generally comprises formation of a mixture of a hydrogel precursor compound, an optional biological material, and a divalent cation. The mixture is then combined with alginate, to generate an alginate shell around droplets of the mixture, followed by gelation of the hydrogel precursor core, and removal of the temporary alginate shell to yield self-sustaining microbeads.

19 Claims, 3 Drawing Sheets (56) References Cited

OTHER PUBLICATIONS

International Search Report and Written Opinion in Corresponding PCT/US15/34041 mailed Aug. 26, 2016 (7 pages).
Morch, et al. "Effect of Ca2+, Ba2+, and Sr2+ on Alginate Microbeads", Biomacromolecules 2006, 7, 1471-1480 (10 pages).
Mazumder, et al. "Core-Cross-Linked Alginate Microcapsules for Cell Encapsulation", Biomacromolecules 2009, 10, 1365-1373 (9 pages).
Nussinovitch, et al. "Liquid-core hydrocolloid capsules", Food Hydrocolloids, 1996, vol. 10 No. 1 pp. 21-26 (6 pages).
Blandino, et al. "Formation of Calcium Alginate Gel Capsules: Influence of Sodium Alginate and CaCl2 Concentration on Gelation Kinetics", Journal of Bioscience and Bioengineering, 1999, vol. 88, No. 6, pp. 686-689 (4 pages).
Koyama, et al. "Cultivation of Yeast and Plant Cells Entrapped in the Low-Viscous Liquid-Core of an Alginate Membrane Capsule Prepared Using Polyethylene Glycol", Journal of Bioscience and Bioengineering, 2004, vol. 97, No. 2, 111-118 (8 pages).
FMC Biopolymer, "Alginates, A World of Possibilities Lies Just Below the Surface", Brochure Copyright 2003, FMC Corporation (20 pages).

\* cited by examiner

MICROENCAPSULATION TECHNIQUE AND PRODUCTS THEREOF

CROSS-REFERENCE TO RELATED APPLICATIONS

The present application claims the priority benefit of U.S. Provisional Patent Application Ser. No. 62/007,717, filed Jun. 4, 2014, entitled MICROENCAPSULATION TECHNIQUE AND PRODUCTS THEREOF, incorporated by reference in its entirety herein.

BACKGROUND OF THE INVENTION

Field of the Invention

The present invention relates to processes and techniques for preparing non-alginate hydrogel microbeads and the resulting products thereof.

Description of Related Art

Cell encapsulation in a hydrogel microparticle is a promising technique in regenerative medicine for two key reasons. First, the structure of the hydrogel matrix is such that encapsulated cells can exchange nutrients and therapeutic molecules with the surrounding environment, while other cell types, namely host immune cells, cannot penetrate and mediate immune rejection of the encapsulated cells when transplanted. Second, hydrogel microparticles are well suited for transplantation of encapsulated cells. Their small physical size and spherical shape allows simple and easy delivery via syringe and needle, rather than an invasive surgical procedure. Furthermore, this small physical size generates minimal resistance of molecular diffusion to and from encapsulated cells, compared with larger, "bulk" gel constructs.

The current methods used for fabricating cell-containing hydrogel microbeads are highly limited. To date, microbeads can only be fabricated using alginate or agarose polymers owing to their unique and simplistic gelation mechanisms. Unfortunately, neither of these materials is desirable with regard to cellular health or function. Many novel hydrogel materials are available that are far superior to alginate or agarose in this respect. However, due to their specific gelation mechanisms, they cannot be prepared as spherical microbeads containing living cells. The present invention provides a method for producing such constructs, and is applicable for a wide variety of hydrogel forming materials.

SUMMARY OF THE INVENTION

Methods of encapsulating biological material in a 3-dimensional hydrogel matrix are described herein. The methods generally comprise providing a hydrogel precursor solution that comprises a hydrogel precursor compound, the biological material, and a divalent cation selected from the group consisting of calcium, barium, strontium, and combinations thereof, dispersed or dissolved in a solvent system. The hydrogel precursor solution is combined with alginate to yield core/shell microparticles. Each of the core/shell microparticles comprises an alginate shell and a liquid core comprising the hydrogel precursor solution. The hydrogel precursor compound in the liquid core is crosslinked to yield core/shell crosslinked microparticles. Each of the core/shell crosslinked microparticles comprises the alginate shell and a core comprising a 3-dimensional hydrogel matrix and the biological material. Advantageously, the biological material is suspended, encapsulated, aka entrapped in the hydrogel matrix. The temporary alginate shell is then removed to yield self-sustaining hydrogel microbeads. Each of the hydrogel microbeads comprises the 3-dimensional hydrogel matrix and biological material entrapped therein.

3-dimensional hydrogel microbeads prepared according to the inventive techniques are also described herein. The microbeads are self-supporting bodies that comprise a 3-dimensional hydrogel matrix and biological material entrapped therein.

A composition for transplantation in a subject is also described herein. The composition comprises a plurality of 3-dimensional hydrogel microbeads prepared according to the inventive techniques. The microbeads are self-supporting bodies that comprise a 3-dimensional hydrogel matrix and biological material entrapped therein.

DETAILED DESCRIPTION

The invention is concerned with an inside-out gelation process to generate hydrogel microcapsules (aka microbeads). More particularly, methods of encapsulating biological material in the microbead 3-dimensional hydrogel matrix are described herein. The process generally comprises formation of a mixture of a hydrogel precursor compound, an optional biological material, and a divalent cation. The mixture is then combined with alginate, to generate an alginate shell around droplets of the mixture, followed by gelation of the hydrogel precursor core, and removal of the alginate shell to yield self-sustaining microbeads.

In one aspect, a hydrogel precursor solution is provided. The hydrogel precursor solution is prepared by dispersing the hydrogel precursor compound in a solvent system to form a solution before mixing with the other components. Preferred solvent systems for the hydrogel precursor solution include water, buffering agents (e.g. histidine, HEPES), density-modifying agents (e.g. iodixanol, ficoll), viscosity-modifying agents (e.g. PEG, carboxymethyl cellulose, xanthan gum), or mixtures thereof. The hydrogel precursor compound will be included in the solution at a level of from about 0.4% to about 4.0% weight/volume (4-40 mg/mL), based upon the total volume of the solution.

Suitable hydrogel precursor compounds include hydrogel-forming polymers, oligomers, and/or monomers, and as such are capable of forming a cross-linked or network structure or matrix (i.e., "hydrogel") through polymerization and/or crosslinking, wherein liquid and biological materials may be retained, suspended, entrapped, and/or encapsulated within the interstitial spaces or pores of the resulting gelled structure or matrix. Hydrogel precursor compounds for use in the invention are preferably non-alginate hydrogel precursor compounds. That is, the hydrogel precursor solution is preferably substantially free of alginate compounds, i.e., compounds based upon alginate, alginic acid, or salts or derivatives thereof. The term "substantially free," as used herein, means that the ingredient is not intentionally added to the composition, although incidental impurities may occur. In such embodiments, the hydrogel precursor solution compositions comprise less than about 0.05% by weight, preferably less than about 0.01%, and more preferably about 0% by weight of such an ingredient, based upon the total weight of the emulsion taken as 100% by weight.

Any crosslinkable hydrogel precursor compounds would be suitable for use with the invention, with preferred compounds being biocompatible non-alginate copolymers, and particularly non-alginate block copolymers, as well as other types of crosslinkable monomers and/or oligomers. Exemplary precursor compounds include, without limitation, non-alginate polysaccharides, modified hyaluronic acid, collagen/gelatin, polyethylene glycol, chitosan, agarose, and the like. A particularly preferred hydrogel precursor compound is hyaluronic acid. In one or more embodiments, the hydrogels are slow-gelling hydrogels. Biocompatible hydrogels are also particularly preferred, depending upon the designated end use of the hydrogel. As used herein, "biocompatible" means that it is not harmful to living tissue, and more specifically that it is not biologically or otherwise undesirable, in that it can be administered to a subject without excessive toxicity, irritation, or allergic or immunogenic response, and does not cause any undesirable biological effects or interact in a deleterious manner with any of the other components of the composition in which it is contained. Biocompatible hydrogels would be selected to minimize any degradation of the biological material and to minimize any adverse side effects in the subject, as would be well known to one of skill in the art. Additional optional ingredients that may be included with the hydrogel precursor include fibronectin, laminin, collagen, other components of the extracellular matrix, and the like, including synthetic versions thereof.

The hydrogel precursor solution further comprises a divalent cation. Suitable divalent cations for use in the invention include any ions capable of forming a gel upon interaction with alginate. More particularly, the divalent cations are preferably biocompatible. In one or more embodiments, the divalent cations are selected from the group consisting of calcium, barium, strontium, and combinations thereof. The divalent cations are dispersed or dissolved in the solvent system along with the hydrogel precursor compound. The divalent cations should be included in the solution at a level of from about 0.025 moles/liter to about 0.25 moles/liter, based upon the total volume of the solution taken as 100%.

The hydrogel precursor solution further comprises a biological material. Exemplary biological materials include populations of cells, cell clusters, tissues, combinations thereof, and fragments thereof. The biological materials can be naturally derived or isolated, or they can be engineered or genetically-modified cells, clusters, tissues or the like. Non-limiting examples of biological materials for use in the invention include islets, islet clusters, hepatocytes, stem cells, and related cells and tissue, as well as endocrine cells, stem cell clusters, thyroid clusters, adrenal gland clusters, pituitary clusters, and other 3-dimensional cell clusters for tissue engineering or cell-based treatments. Combinations of cell types and/or tissues could also be used in the invention.

In one or more embodiments, additional additives, media, nutrients, pH buffers, density modifying agents, viscosity modifying agents, or the like can be included in the hydrogel precursor solution. In some embodiments, the hydrogel precursor solution consists essentially or even consists of the hydrogel precursor compound, divalent cation, and biological materials, dispersed or dissolved in the solvent system. The hydrogel precursor solution remains is in liquid form until gelation as described below, and as such, in one or more embodiments, the solution is preferably essentially free of hydrogel crosslinking agents. In one or more embodiments, the density of the hydrogel precursor solution is "matched" to the density of the biological material to improve the ability maintain the biological material suspended throughout the hydrogel precursor solution (and throughout the resulting droplet, discussed below). Thus, in some embodiments, it may be desirable to increase the viscosity of the hydrogel precursor sufficiently in order to slow or prevent migration or "settling" of the biological material to the edge of the liquid core prior to gelation/crosslinking, as discussed in more detail below.

The hydrogel precursor solution is then combined with alginate. In one or more embodiments, the hydrogel precursor solution is added dropwise to a solution of alginate to form an alginate shell on individual droplets of the hydrogel precursor solution. For example, the liquid hydrogel precursor solution is extruded or dispensed from a suitable apparatus for forming droplets. Any suitable apparatus can be used, and will generally comprise a chamber for holding the hydrogel precursor solution, with the chamber being in fluid communication with a fluid passage that terminates in a dispensing outlet or tip. The dispensing tip will have an orifice through which the hydrogel precursor solution is expelled as a droplet. The technique can be executed using a simple apparatus, such as a syringe and needle, as well as machines specifically designed for droplet generation. The desired size of the droplet can be controlled based upon the cross-sectional dimension of the orifice, the viscosity of the hydrogel precursor solution, and relative viscosity of the alginate solution. The invention is particularly suited for droplets having a maximum surface-to-surface dimension (i.e., in the case of a spherical droplet, its diameter) of less than about 5 mm, preferably less than about 2 mm, more preferably less than about 1 mm, and even more preferably ranging from about 50 µm to about 750 µm.

In general, the solution of alginate will comprise a sodium alginate bath, and preferably an agitated or stirring bath of sodium alginate dispersed in a solvent system. Other alginate salts (besides calcium alginate) could be used. Various types of gel-forming, but decrosslinkable, alginates can be used in the invention depending on the desired properties. In general, low viscosity/low molecular weight and high-G alginates are preferred, such as those extracted from *Laminaria hyperborea*. Alginates are commercially available according to their different properties from various sources, including FMC BioPolymer (Philadelphia, Pa.). The amount of alginate in the solution can be varied, but can range from about 0.1% to about 2.0% weight/volume, based upon the total volume of the solution taken as 100%. In general, the viscosity of the alginate solution should be less than the viscosity of the hydrogel precursor solution. The viscosity of an alginate solution depends upon the alginate concentration and average molecular weight of the alginate polymer (i.e., length of alginate molecules or number of monomer units in the chains), with longer chains resulting in higher viscosities at similar concentrations. In one or more embodiments, the viscosity of the alginate solution will range from about 1 to about 20 cP, and preferably from about 1 to about 4 cP at room temperature (~20 to 25° C.). More specifically, the ratio of viscosity of the hydrogel precursor solution to the viscosity of the alginate solution should be greater than 1 at room temperature. In one more embodiments, the ratio of viscosity of the hydrogel precursor solution to the viscosity of the alginate solution is from about 1:1 to about 1000:1. In one or more embodiments, the ratio of viscosity of the hydrogel precursor is about 20:1. In one or more embodiments, the viscosity of the hydrogel precursor solution is from about 1 up to about 500 cP, with about 40 to about 100 cP at room temperature being particularly preferred.

Advantageously, the divalent cation in the hydrogel precursor solution reacts with the alginate to yield a core/shell microparticle for each droplet comprising an alginate shell and a liquid core comprising the hydrogel precursor solution. The core/shell microparticles can be placed in an additional solution containing divalent cation if further hardening of the alginate shell is desired. Regardless it will be appreciated that this approach has a significant advantage in that it creates a temporary (removable), porous, and substantially spherical mold or encapsulant for containing the hydrogel precursor solution. As will be appreciated, "substantially spherical" means that the core/shell microparticle may be spherical with a more "regular" shape, or may have a more irregular shape (ellipsoidal, oblong, etc.).

It will be appreciated that for successful encapsulation by the alginate shell, the droplet "cores" must penetrate the surface of the alginate solution after being dispensed. That is, the droplets must have sufficient velocity and/or momentum to break the surface tension of the alginate solution. Those skilled in the art will recognize that several variables can be manipulated to achieve the desired outcome. For example, the alginate solution can be agitated or stirred to reduce the surface tension of the solution. Similarly, it will be appreciated that the relative viscosities of the droplet and the alginate bath can be adjusted to facilitate droplet entry into the alginate bath. Likewise, the requisite droplet velocity will be reduced for larger-sized droplets (i.e., droplets having more mass, thus giving rise to adequate momentum at lower velocity). The height from which the droplets are dispensed can also be varied. In one or more embodiments, the droplets are dispensed from a height (as calculated from the surface of the alginate solution to the dispensing tip) of from about 15 to about 20 cm. In one more embodiments, the target velocity for the droplets is from about 1.5 m/s to about 5 m/s, and preferably from about 1.5 m/s to about 4 m/s.

The hydrogel precursor compound in the liquid core is then crosslinked to yield core/shell crosslinked microparticles. Crosslinking can be carried out by various mechanisms depending upon the particular hydrogel precursor compound. In one or more embodiments, the core/shell microparticles are combined with a hydrogel matrix crosslinker, preferably in solution. The crosslinker leaches through the alginate shell into the core/shell microparticles resulting in gelation (crosslinking) of the hydrogel precursor compound to form a 3-dimensional hydrogel matrix. The crosslinker will correspond to the hydrogel precursor compound, but can be varied to control the speed and level of crosslinking achieved within the resulting crosslinked matrix. Suitable crosslinkers include photo- or thermal-initiated crosslinkers, chemical crosslinkers, such as PEG-based crosslinkers (e.g., PEGDA), and the like. Self-crosslinking hydrogel precursors could also be used.

It will also be appreciated that a hydrogel crosslinker could be dissolved in the initial alginate bath in order to facilitate somewhat simultaneous hydrogel gelation and formation of the alginate shell in "one-step" without having to transfer the microparticles to a separate container for hydrogel crosslinking. Likewise, the hydrogel crosslinking agent could actually be included in the initial hydrogel precursor solution at a designated pH (e.g., pH<7) in order to effectively pause gelation, whereas the alginate bath could be prepared at pH 8, which significantly reduces gelation time of the hydrogel precursor. Similarly, a photo-crosslinkable hydrogel system can be used, which would involve exposing the core/shell microparticle to activating radiation (e.g., UV light) to initiate hydrogel formation in the liquid cores.

It will also be appreciated that different crosslinkers could be used to change the speed of gelation/crosslinking. The data present indicate that even a large (e.g., 3400 Dalton PEG) crosslinkers are capable of diffusing through the alginate shell and reacting with the hydrogel precursor compound to initiate gelation.

Regardless of the gelation mechanism used, each core/shell crosslinked microparticle will comprise a distinct alginate shell and now-solidified or "gelled" core comprising a 3-dimensional hydrogel matrix with the biological material suspended, entrapped, or encapsulated in the hydrogel matrix. It will be appreciated that this approach has a significant advantage in that it permits gelation of the hydrogel precursor solution within the porous mold under physiological conditions. The resulting hydrogel matrix is characterized as being a semi-rigid network that is permeable to liquids and gases, but which exhibits no flow and retains its integrity in the steady state. The hydrogel matrix is a 3-dimensional self-sustaining body. The term "self-sustaining body" means that the hydrogel matrix, once formed, retains its shape without an external support structure, and is not susceptible to deformation merely due to its own internal forces or weight. The self-sustaining body is not pliable, permanently deformable, or flowable, like a jelly, putty, or paste, but is resilient, such that the matrix body may temporarily yield or deform under force. In other words, the self-sustaining body will recoil or spring back into shape after minor compression and/or flexing—it being appreciated that the hydrogel matrix will crack, break, or shear under sufficient exertion of external pressure or force.

The alginate shell is then removed from the core/shell crosslinked microparticles to yield self-sustaining hydrogel microbeads. In one or more embodiments, the core/shell, crosslinked microparticles are contacted with an appropriate chelating agent, preferably in solution, and for a sufficient period of time to weaken, dissolve, or otherwise disrupt (and thereby remove) the alginate shell. Preferably, the core/shell, crosslinked microparticles are contacted with the appropriate chelating agent under agitation or stirring. Exemplary chelators include citrate, as well as other known chelating agents for the divalent cations (e.g., calcium, barium, or strontium), such as EDTA (ethylene diamine tetraacetic acid), EGTA (ethylene glycol tetraacetic acid), phosphates (e.g., orthophosphate, phosphate salts, etc.), and the like. Additionally, the divalent cation used in formation of the alginate shell could be displaced (albeit very slowly) over time in a saline solution containing, for example, very low calcium concentrations. The alginate shell could also be broken and dislodged using mechanical agitation of the microparticles. The core/shell, crosslinked microparticles can also be collected on a screen or strainer and washed with additional chelator solution if desired, until the alginate shell is removed.

Regardless of the embodiment, removal of the alginate shell yields a hydrogel microbead comprising the biological constituent encapsulated, entrapped, or suspended within the 3-dimensional hydrogel matrix. It will be appreciated that this approach has a significant advantage in that it permits dissolution and removal of the porous spherical mold under physiological conditions after successful gelation of hydrogel matrix. The resulting hydrogel microbead is a 3-dimensional (e.g., substantially spherical) matrix-type capsule, meaning that it holds the fill material throughout the bead, rather than having a distinct shell as in a core-shell type capsule. As noted above, the hydrogel microbead is also a self-sustaining body. The resulting hydrogel microbeads can be collected from the solution using a mesh screen or other device, and may be rinsed or suspended in medium or appropriate nutrients, as desired. In one or more embodiments, the resulting microbeads are substantially spherical in shape. Advantageously, the particle size is highly customizable depending upon the capabilities of the selected droplet generator. In one or more embodiments, the resulting hydrogel microbeads or microparticles have an average (mean) maximum surface-to-surface dimension (i.e., in the case of a spherical microbead, its diameter) of less than about 5 mm, preferably less than about 2 mm, more preferably from about 50 µm to about 2 mm, even more preferably ranging from about 50 µm to about 750 µm, and most preferably from about 50 µm to about 500 µm.

It will be appreciated that the microbeads or particles formed during the above process may be filtered and/or washed between various steps in the process to isolate the microbeads or particles from the formation solution before proceeding to the next step.

In summary, the method described herein allows for the fabrication of non-alginate hydrogel microspheres under biologically relevant conditions. Microencapsulation of living cells or tissue has very broad appeal in tissue engineering and cell-based therapy, yet the materials currently able to be formulated as microcapsules is essentially limited to alginate and in some cases agarose, neither of which possess important biological cues to support or direct cell function. Thus, an important feature of this method is for the microencapsulation of cells or cell clusters in non-alginate hydrogel materials to improve biological activity and biocompatibility. Additionally, alternative material choices (e.g. covalently cross-linked hydrogels, variable cross-linker sizes and reaction chemistry, etc.) could potentially enable a much greater level of control of structural, mechanical, and degradation properties of the resulting microcapsules. Advantageously, because of the temporary alginate shell, microcapsules can be created even when using slow-gelling hydrogel precursors.

Another key advantage is that the process is compatible with cells, in contrast to other microsphere fabrication methods that use organic solvents or are otherwise toxic to living tissues. Additional benefits of the described methods include that the hydrogel microbeads improve biocompatibility of the implanted biological material, reducing fibrosis. In addition, the microbeads allow for enhanced control and support of cell and tissue function in the microbeads, improving the bioactivity of any implants created using such microbeads. Furthermore, use of the temporary alginate shell permits a wider variety of hydrogels to be used to create the microbeads, which allows the skilled artisan more control over the desired mechanical properties of the results microbead (e.g., elastic modulus, toughness, etc.). Furthermore, this technique also permits the skilled artisan to selected hydrogels based upon other desired characteristics, such as to control the degradation rate of the hydrogel, once implanted (e.g., by being able to choose between covalent vs. ionic cross-linked gels for long term immunoprotection (cell transplant therapy) or short term cell support (tissue engineering)). Similarly, by being able to select among a range of hydrogels, but still form microbeads, the skilled artisan also has more control of the desired microstructure of the hydrogel matrix, such as the pore size and diffusional properties of the resulting microbeads.

The resulting hydrogel microbeads have various uses, including, without limitation reversal of diabetes via encapsulated islets or islet cells, delivery of modified cells or stem cells for bone or cartilage repair, protection of transplanted therapeutic cells or cell clusters from host immune system in general.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Background work was carried out to evaluate liquid core alginate capsules. Briefly, a solution of 40% glucose and 25 or 50 mM calcium chloride was dropped into low viscosity sodium alginate at various concentrations. Glucose was used to increase the viscosity and density of the liquid core solution, which appears to be necessary in order to form spherical constructs. Calcium was dissolved into the liquid core solution to initiate rapid gelation of the alginate once the drop entered the alginate bath in an inside-out gelation mechanism. Results of the glucose experiments showed clear, smooth interfaces of the liquid core and alginate shell. However, the constructs observed, while generally round, possessed tail like features. This was most likely due to non-optimal rheological properties. The liquid core constructs were then exposed to 50 mM sodium citrate and mildly agitated to assess whether the alginate shells could be dissolved using physiologically relevant concentrations of citrate. Indeed, the alginate shells eventually dissolved, leaving no observable trace of gelled constructs (the liquid glucose core simply dissolved back into the bulk solution).

Figure 1:
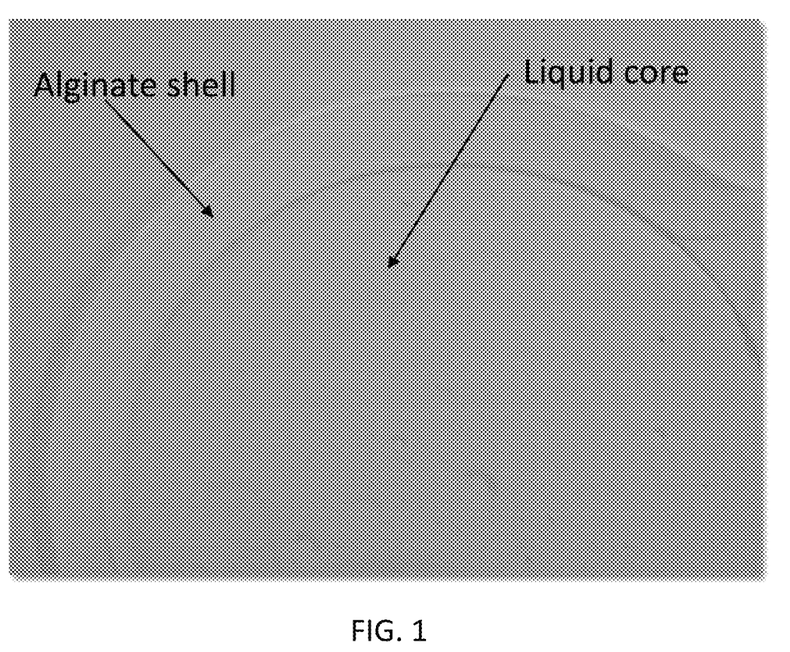
FIG. 1 is a microscope image of a core/shell microparticle with the alginate shell and a liquid core comprising the hydrogel precursor solution from Example 1.

After having identified acceptable reagent concentrations and general technique, a commercially-available HA hydrogel (HyStem) was used as the liquid core solution. Due to its greater viscosity (exact metric unknown), only the hyaluronic acid component, Glycosil, was used to increase the likelihood of success in this experiment. GMP-grade Glycosil was dissolved in HTK solution at 1× (2 mL), and then added to a vial containing calcium chloride so as to achieve a final liquid core solution of 1× Glycosil and 25 mM calcium chloride (HTK solution as solvent). This was added drop-wise through a 27 G blunt tip needle into a stirred 0.25% sodium alginate bath (Protanal LF 10/60, low viscosity, high G content) from a height of 1-2 cm. Generally spherical dual-layered constructs formed in the alginate bath. See FIG. 1. Most appeared to have small tail-like features, similar to those observed in the glucose experiments. However, a small percentage of the constructs appeared significantly spherical without any visible tail, which may indicate the rheological properties of this particular formulation are close to, but not quite appropriately tuned for this technique.

The liquid core-shell constructs were left stirring for 5 minutes and then collected with a 250 uM nylon mesh screen, and transferred to PBS containing ~10 mM calcium chloride to strengthen the alginate shell to protect the integrity of the construct during core hardening.

Constructs were later transferred to a vial containing the HyStem crosslinker, PEGDA, at 1× concentration (i.e. 1 vial in 2.5 mL total volume) to recreate normal cross-linker concentration. PEGDA (3400 Dalton) permeates both the alginate shell and the HyStem core, allowing the cross-linker to eventually diffuse throughout the construct. This parameter is clearly subject to variation, as the ratio of total PEGDA to HyStem components was much higher than if the gel were to be made in bulk. In this case, only a couple hundred microliters of Glycosil was in the container, rather than the normal 2.0 mL of Glycosil+Gelin-S. Regardless, this was simply chosen as a starting point, and can be modified.

Figure 2:
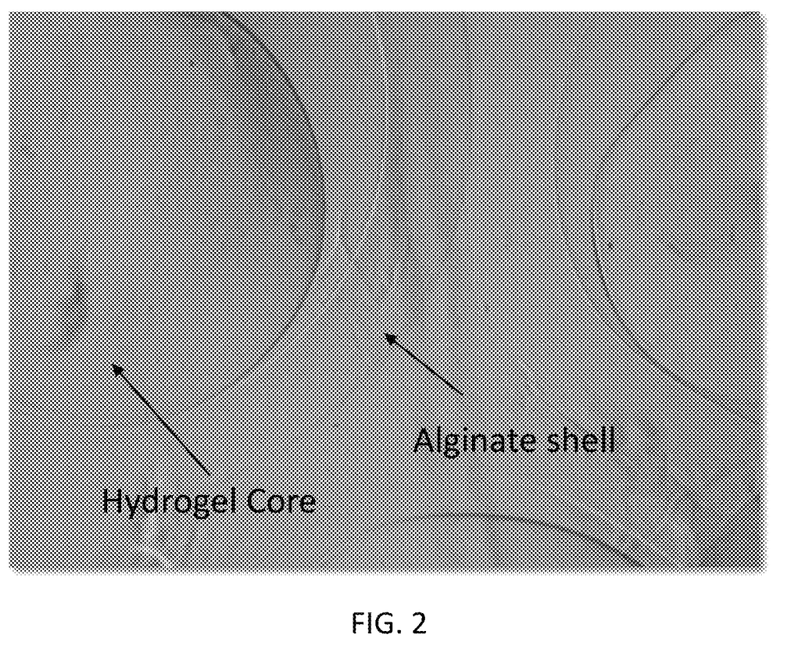
FIG. 2 is a microscope image of a core/shell crosslinked microparticle with the alginate shell and hydrogel core from Example 1.
Figure 3:
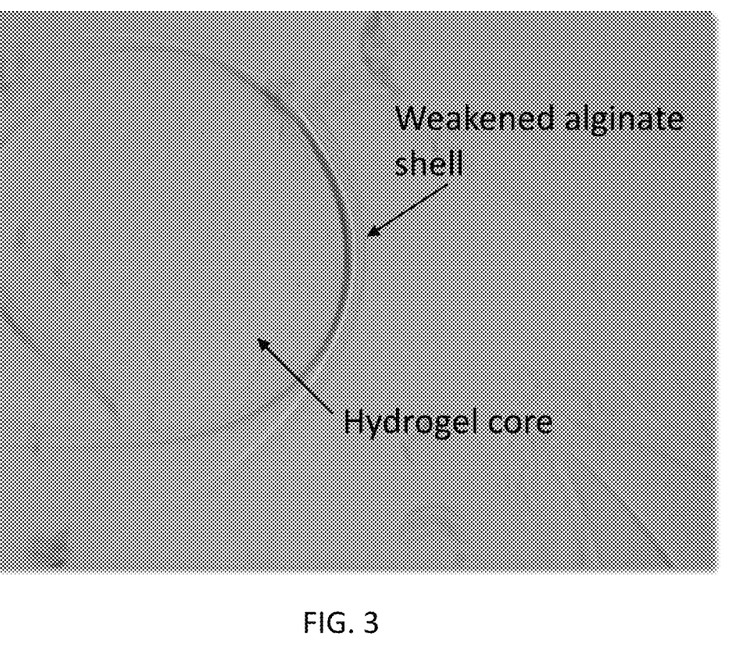
FIG. 3 is a microscope image of a core/shell crosslinked microparticle after 20 minutes in citrate from Example 1.
Figure 4:
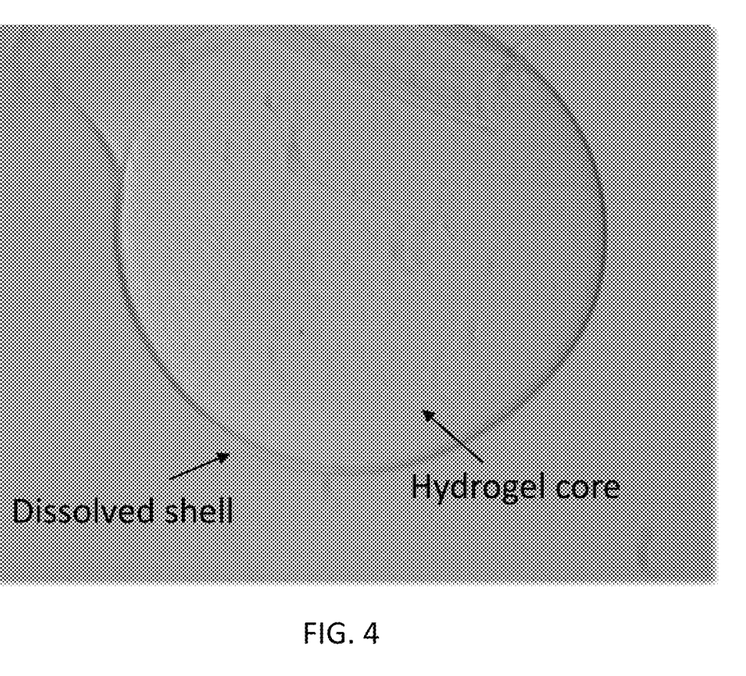
FIG. 4 is a microscope image of a core/shell crosslinked microparticle after 45 minutes in citrate from Example 1.
Figure 5:
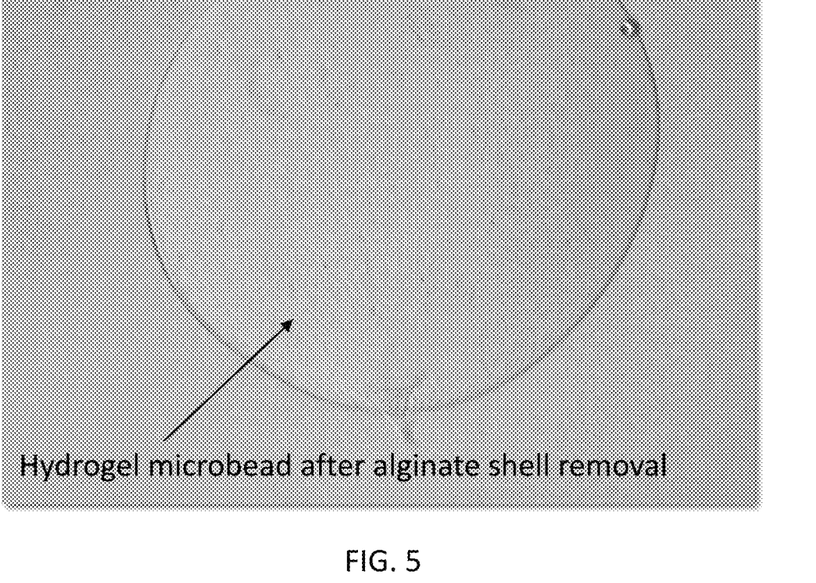
FIG. 5 is a microscope image of the microbeads after shell removal.
Figure 6:
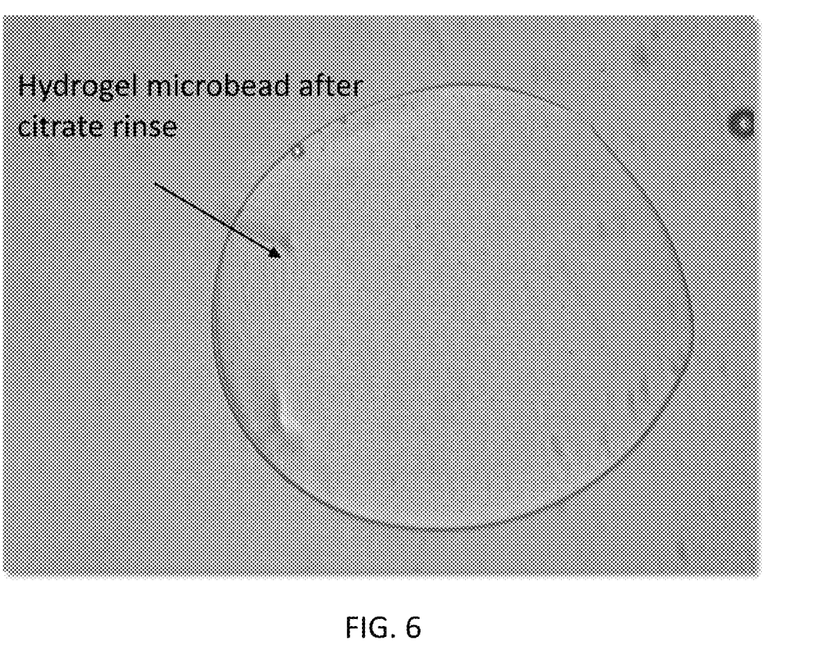
FIG. 6 is a microscope image of the microbeads after a final citrate rinse, showing only the hydrogel core remaining from Example 1.

After incubation at room temperature over the weekend, the constructs were observed via light microscopy. The resulting constructs are shown in FIG. 2. Interestingly, it appeared as though either the cores shrunk, or the shells expanded, as there were void spaces between the two layers that were originally in direct contact. The constructs were transferred to a petri dish containing 10 mL of 50 mM sodium citrate in PBS and placed on an orbital shaking at low rpm to create mild agitation and fluid flow. Constructs were observed for 45 minutes, during which time the alginate shells significantly deteriorated and in some cases completely disappeared and the HyStem cores remained unchanged, and in their original spherical geometry. See FIG. 3. After 45 minutes, constructs (see FIG. 4) where collected in a 250 uM nylon mesh screen, returned to the petri dish and rinsed with a fresh 10 mL aliquot of 50 mM sodium citrate. See FIG. 5. Not long after this step (a matter of minutes), virtually all constructs where devoid of any visible shell, with only the hardened HyStem cores remaining. See FIG. 6.

The HyStem microspheres were then transferred to clean PBS for further observation.

Example 2

A. General Protocol to Produce Hydrogel Microspheres Using an Alginate Mold

1. Prepare liquid hydrogel polymer solution at desired final component concentrations, adjusted to contain 25 mM calcium ion. The cation concentration should be adjusted for different droplet sizes. For example, up to 200 mM calcium ion and/or 200 mM barium ion has been used for droplets with an average size range of from about 400-600 microns.

2. Load solution into droplet generator (e.g., syringe/needle, or a microparticle/microencapsulator device) and initiate droplet formation, adjusting instrument settings to achieve desired drop size.

3. Collect droplets in stirring bath containing a solution of 0.25% low viscosity sodium alginate (w/v) in a calcium free buffer or medium (e.g. PBS) at room temperature. The alginate concentration can be adjusted. For example, 0.125% w/v sodium alginate has been used for smaller droplets. The viscosity and density of the hydrogel polymer (core) solution ultimately dictates whether or not truly spherical constructs can be formed upon contact with the alginate bath. Beyond this, the drop height, i.e. the distance from the droplet-generating outlet to the surface of the bath will also play a role in the morphology of the resultant constructs. The specific values of these parameters will also vary depending the size of the droplet, the type of material, concentration and viscosity of the alginate solution, etc. These factors must be considered and will ultimately place constraints on the composition of the target hydrogel polymer solution.

4. Upon collection of all droplets in the bath, continue stirring for ~5 min to allow alginate shells to fully form and reduce or prevent aggregation of liquid core-shell constructs. Depending on the size (volume) of the original droplet, this step may be optional. For larger spheres (1-3 mm), doing this did appear to limit aggregation of the constructs. The length of stirring is inversely proportional to the divalent cation concentration used in the droplets. In addition, it has been found that droplet deformation can occur with excessive stirring. A stirring time of about 1-2 minutes has been found sufficient for smaller droplets.

5. Separate constructs from alginate solution using an appropriately sized strainer or screen.

6. Cross-link/gel the core hydrogel polymer solution according to the specific requirement of the particular hydrogel solution being used. This step will vary depending upon the type of hydrogel precursor solution used. In some cases it will involve transferring the liquid core-shell constructs to a core gelling bath or vessel containing hydrogel crosslinker. Regardless, it is likely that this step will be very similar to the manufacturer's recommended gelation protocol associated with each material, with only slight modifications to account for the alginate shell and construct geometry. Whatever the case, the medium used herein should contain at least some amount calcium ion to maintain the integrity of the alginate shell during hardening.

7. Any further desired hardening, curing, or incubation could be done at this point (e.g. if encapsulating living cells that require gentle handling). Otherwise, proceed immediately to step 8.

8. The temporary alginate shell is then removed. For example, the core/shell constructs are then transferred to a bath and/or washed with appropriate chelator to remove the alginate shell. Transfer the now solid core-shell constructs to a solution of 25-50 mM sodium citrate in PBS (or other calcium free buffer), and mildly agitate for 20-40 minutes at 24-37° C., while visually monitoring the progress of shell degradation. The specific volume ratio of microspheres to citrate solution has not been identified. Given the very low cost of citrate, this step should simply be done using a rather large excess of the citrate solution to ensure complete removal of the alginate shell.

9. Rinse constructs using appropriately sized strainer or screen with additional citrate solution, repeat agitation in fresh citrate solution until shells fully dissolved by visual inspection. It is likely that the mechanical shear of the fluid during rinsing is why this step was effective in removing the remaining alginate shell material, rather than the "fresh" citrate solution. Thus, performing this rinsing step earlier could potentially shorten this process.

10. Microspheres (microbeads) are now ready to be used. Transfer to desired medium or buffer for use.

B. Example Procedure Used to Produce "HyStem" Microspheres Using Alginate Mold Method 1. GMP grade Glycosil (the thiolated hyaluronic acid polymer component of HyStem-C hydrogels) was reconstituted at 10 mg/mL using a buffered organ preservation solution. The solution is HTK Preservation Solution.

2. Calcium chloride powder was added to the Glycosil solution to achieve ~25 mM calcium ion concentration.

3. The Ca2+/Glycosil hydrogel polymer solution was then added dropwise to a stirring 0.25% (w/v) alginate bath (Protanal LF 10/60) using a syringe and 27 G blunt tipped needle from a height of 1-2 cm. At times, in order to decrease the droplet size, the droplet was mechanically disturbed be tapping the syringe.

4. Spherical liquid Glycosil core-alginate shell constructs formed instantly upon contact of the droplet with the bath, and were stirred for an additional 5 minutes to allow the shell to fully form and reduce aggregation. While generally spherical, constructs did have tail-like features, some larger than others. These should be easily eliminated by adjusting the viscosity of the Glycosil solution, e.g. concentration, or addition of other viscosity modifying agents.

5. Constructs were collected with a 250 micron nylon mesh screen and stored in 10 mM Ca2+ in PBS for later processing (shell removal). This step may be optional in some cases.

6. Constructs were transferred to a tube containing Extralink (3400 g/mol PEG Diacrylate) at a final concentration of 1× (i.e. 1 vial of GMP grade Extralink in 2.5 mL in said buffered solution used in step 1), and incubated at room temperature for 2 days. Shorter incubation times may be used in certain embodiments.

7. The constructs were then transferred to a solution of 50 mM sodium citrate in PBS and agitated gently on an orbital shaker for ~45 minutes. Alginate shell degradation was monitored via light microscopy. Not much change was noticed between 20-45 minutes. As alluded to in the general protocol commentary, the rinsing step appeared to facilitate the shell removal process.

8. Constructs were then rinsed in a 250 micron nylon mesh screen with fresh citrate solution, then further agitated in sodium citrate until no visual evidence of the alginate shell remained, leaving only the solid spherical Glycosil core. It is possible that the alginate was completely removed by the rinsing step alone. However, this was not verified via microscopy prior to being returned to the citrate solution and agitated for several minutes.

9. Glycosil spheres were stored in PBS at room temperature.

C. Example Procedure Used to Produce "HyStem" Microspheres Using Alginate Mold Method with Crosslinker in Hydrogel Precursor 1. The hydrogel precursor solution was prepared as follows: 1% w/v Glycosil (thiolated HA, MW ~250 kDa), 200 mM Calcium Chloride, 100 mM Histidine, and 0.25% PEGDA 3400 (pH 6.5, viscosity ~50 cP).

2. Droplets of hydrogel precursor approximately 600 microns in diameter were dropped into a stirring bath of 0.125% Protanal LF 10/60 Low Viscosity Alginate (viscosity ~2.5 cP) from a height of 17 cm with an initial velocity of approximately 1.5 m/s at room temperature to form core/shell microparticles.

3. The core shell microparticles were stirred in the alginate bath for 2 minutes, and were then collected using a 250 micron screen.

4. Core/shell microparticles were transferred to PBS (pH 7.4) and incubated overnight to permit crosslinking of the hydrogel (Glycosil and PEGDA).

5. After overnight incubation, the core/shell microparticles were transferred to a stirring bath of 0.85% sodium chloride (or calcium free PBS) containing 50 mM sodium citrate until alginate shells were completely dissolved.

Example 3

A. Example Procedure Used to Produce UV-Crosslinked "HyStem-C" Microspheres Using Alginate Mold Method 1. The hydrogel precursor solution was prepared with the following composition and physical properties.
   1.0% (w/v) Glycosil (hydrogel precursor polymer)
   0.5% (w/v) Gelin-S (bioactive agent)
   1.0% (w/v) 4-Arm Polyethylene glycol norbornene (hydroxyl radical catalyzed thiol reactive crosslinker, MW: 10 kDa, JenKem USA)
   12% (v/v) iodixanol (density modification agent)
   200 mM $CaCl_2$
   10 mM HEPES
   pH~7 at room temperature
   Density=1.08 g/mL at room temperature
   Viscosity ~60 cP at room temperature 2. The alginate bath was prepared with the following composition and physical properties.
   0.12% (w/v) Protanal LF 10/60 Low Viscosity Alginate
   0.1% Tween 20 (surfactant)
   0.1% Irgacure 2959 (photoinitiator, Sigma Aldrich)
   10 mM HEPES
   pH~7 at room temperature
   Density ~1.0 g/mL at room temperature
   Viscosity ~2.5 cP at room temperature 3. Droplets of the hydrogel precursor solution were introduced into the stirred alginate bath using droplet generator from a height of approximately 20 cm to generate core/shell microparticles of approximately 1 mm core diameter.

4. Immediately following core/shell particle formation, the stirred bath was irradiated with a longwave ultraviolet lamp (Ultraviolet Products, LLC, Model UVL-56, 6 Watts, 365 nm) through the sidewall of the glass vessel containing the particles and alginate solution with the photoinitiator (Irgacure 2959). Stirring was continued for 5 minutes.

5. After 5 minutes of initial stirring, the alginate bath was diluted 1:1 with saline containing 10 mM HEPES to prevent aggregation and overgrowth of the alginate shells. UV irradiation and stirring was continued for 25 additional minutes.

6. Finally, 1.0 M sodium citrate was added to the bath to a final concentration of 25 mM citrate ion. The alginate shells fully dissolved after about 5 minutes to reveal crosslinked HyStem hydrogel microbeads. HyStem beads were then collected using a 250 micron screen.

What is claimed:

1. A method of encapsulating biological material in a 3-dimensional hydrogel matrix, said method comprising:
    providing a hydrogel precursor solution, said solution comprising a hydrogel precursor compound, said biological material, and a divalent cation selected from the group consisting of calcium, barium, strontium, and combinations thereof, dispersed or dissolved in a solvent system;
    combining said hydrogel precursor solution with alginate to initiate gelation of said alginate and yield core/shell microparticles, each core/shell microparticle comprising an alginate shell and a liquid core comprising said hydrogel precursor solution;
    crosslinking said hydrogel precursor compound in said liquid core to yield core/shell crosslinked microparticles, each core/shell crosslinked microparticle comprising said alginate shell and a core comprising a 3-dimensional hydrogel matrix and said biological material, said biological material being entrapped in said hydrogel matrix; and
    removing said alginate shell to yield self-sustaining hydrogel microbeads, each hydrogel microbead comprising said 3-dimensional hydrogel matrix and biological material entrapped therein.

2. The method of claim 1, wherein said hydrogel precursor compound is a non-alginate compound.

3. The method of claim 1, wherein said hydrogel precursor compound is hyaluronic acid.

4. The method of claim 1, wherein said hydrogel precursor solution further comprises fibronectin, laminin, collagen, extracellular matrix components, or synthetic versions thereof.

5. The method of claim 1, wherein said biological material is selected from the group consisting of populations of cells, cell clusters, tissues, combinations thereof, and fragments thereof.

6. The method of claim 1, wherein, said biological material is selected from the group consisting of islets, hepatocytes, stem cells, endocrine cells, tissues related to islets, hepatocytes, stem cells, endocrine cells, and islet clusters, hepatocyte clusters, stem cell clusters, thyroid clusters, adrenal gland clusters, pituitary clusters, and combinations thereof.

7. The method of claim 1, wherein said hydrogel precursor solution consists essentially said hydrogel precursor compound, divalent cation, and biological material, dispersed or dissolved in the solvent system.

8. The method of claim 1, wherein said hydrogel precursor solution further comprises an optional hydrogel crosslinking agent.

9. The method of claim 1, wherein said alginate is sodium alginate.

10. The method of claim 1, wherein said combining comprises adding said hydrogel precursor solution dropwise to a solution of alginate to yield said core/shell microparticles.

11. The method of claim 10, wherein said adding comprises generating droplets of said hydrogel precursor solution and dropping said droplets into said solution of alginate to yield said core/shell microparticles.

12. The method of claim 11, wherein said droplet has a maximum surface-to-surface dimension of less than about 5 mm.

13. The method of claim 10, wherein the ratio of viscosity of the hydrogel precursor solution to the viscosity of the alginate solution is greater than 1 at room temperature.

14. The method of claim 1, wherein said crosslinking comprises contacting said core/shell microparticles with a hydrogel matrix crosslinker.

15. The method of claim 1, wherein said crosslinking comprises exposing said core/shell microparticles to activating radiation to initiate crosslinking.

16. The method of claim 1, wherein said removing comprises contacting said core/shell, crosslinked microparticles with a chelating agent to weaken, dissolve, or disrupt said alginate shell.

17. The method of claim 16, wherein said chelating agent is selected from the group consisting of citrate, EDTA, EGTA, phosphates, and mixtures thereof.

18. The method of claim 1, wherein said removing comprises physically agitating said core/shell, crosslinked microparticles to break said alginate shell.

19. The method of claim 1, wherein said hydrogel microbead has a maximum surface-to-surface dimension of less than about 5 mm.

* * * * *